(12) United States Patent
Everett et al.

(10) Patent No.: US 10,557,860 B2
(45) Date of Patent: Feb. 11, 2020

(54) CIRCULATING PULMONARY HYPERTENSION BIOMARKER

(71) Applicant: THE JOHNS HOPKINS UNIVERSITY, Baltimore, MD (US)

(72) Inventors: Allen D. Everett, Glenwood, MD (US); Jun Yang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/505,317

(22) PCT Filed: Aug. 21, 2015

(86) PCT No.: PCT/US2015/046251
§ 371 (c)(1),
(2) Date: Feb. 21, 2017

(87) PCT Pub. No.: WO2016/029091
PCT Pub. Date: Feb. 25, 2016

(65) Prior Publication Data
US 2017/0269106 A1   Sep. 21, 2017

Related U.S. Application Data

(60) Provisional application No. 62/040,266, filed on Aug. 21, 2014.

(51) Int. Cl.
*G01N 33/74* (2006.01)
*G01N 33/68* (2006.01)

(52) U.S. Cl.
CPC ..... *G01N 33/74* (2013.01); *G01N 2333/4753* (2013.01); *G01N 2800/12* (2013.01); *G01N 2800/52* (2013.01)

(58) Field of Classification Search
CPC ............... G01N 33/74; G01N 33/6893; G01N 2333/475; G01N 2800/12; G01N 2800/52
See application file for complete search history.

(56) References Cited

U.S. PATENT DOCUMENTS

| 2006/0154278 A1 | 7/2006 | Brody et al. | |
| 2011/0119776 A1 | 5/2011 | Wong et al. | |
| 2017/0131289 A1* | 5/2017 | Zisman | G01N 33/6827 |

FOREIGN PATENT DOCUMENTS

EP    2607494 A1    6/2013

OTHER PUBLICATIONS

Dayarian, Adel et al. "Predicting protein phosphorylation from gene expression: top methods from the IMPROVER species translation challenge." Bioinformatics (2015) 31 462-470. (Year: 2015).*
Everett et al. Hepatoma-derived growth factor stimulates smooth muscle cell growth and is expressed in vascular development. 2000, J. Clin. Invest. 105:567-575.
Everett et al. Nuclear Targeting is Required for Hepatoma-derived Growth Factor-stimulated Mitogenesis in Vascular Smooth Muscle Cells. 2001, J. Biol. Chem. 276:37564-37568.
Everett et al. Hepatoma-derived growth factor is a pulmonary endothelial cell-expressed angiogenic factor. American Journal of Physiology-Lung Cellular and Molecular Physiology, 2004, vol. 286, No. 6, pp. L1194-L1201.
Mori et al. Hepatoma-derived growth factor is involved in lung remodeling by stimulating epithelial growth. American Journal of Respiratory Cell and Molecular Biology, 2004, vol. 30, No. 4, pp. 459-469.
Ren et al. Expression of Hepatoma-Derived Growth Factor is a Strong Prognostic Predictor for Patients With Early-Stage Non-Small-Cell Lung Cancer. 2004, J. Clin. Oncol. 22:3230-7.
Okuda et al. Hepatoma-derived growth factor induces tumorigenesis in vivo through both direct angiogenic activity and induction of vascular endothelial growth factor. 2005, Cancer Science 94:1034-1041.
Narron et al. Hepatoma-Derived Growth Factor is Expressed after Vascular Injury in the Rat and Stimulates Smooth Muscle Cell Migration. 2006, Peds. Res. 59:778-783.
Souza et al. NT-proBNP as a tool to stratify disease severity in pulmonary arterial hypertension. 2007, Resp. Med. 101:69-75.
Zheng et al. Development and clinical evaluation of a multi-purpose mAb and a sandwich ELISA test for hepatoma-derived growth factor in lung cancer patients, Journal of Immunological Methods, 2010, vol. 355, pp. 61-67.

* cited by examiner

*Primary Examiner* — Christopher Adam Hixson
(74) *Attorney, Agent, or Firm* — Johns Hopkins Technology Ventures

(57) ABSTRACT

Methods and kits for determining, predicting, or diagnosing pulmonary artery hypertension (PAH) and for determining the efficacy of PAH therapy using biomarkers are provided.

12 Claims, 8 Drawing Sheets
Specification includes a Sequence Listing.

Proteomic discovery: Lung and Plasma Proteins with Significant changes between PAH and control

| Protein Name | Control | APAH | APAH/Control (Fold Change) | IPAH | IPAH/Control (Fold Change) | Plasma IPAH/Control |
|---|---|---|---|---|---|---|
| Hepatoma derived growth factor (HDGF) | 1.0 | 4.0 | 4.0 | 4.0 | 4.0 | 43 |

SEQUENCE LISTING

<160> NUMBER OF SEQ ID NOS: 1

<210> SEQ ID NO 1
<211> LENGTH: 16
<212> TYPE: PRT
<213> ORGANISM: Homo sapiens

<400> SEQUENCE: 1

Ala Lys Glu Glu Ala Glu Ala Pro Gly Val Arg Asp His Glu Ser Leu
1               5                   10                  15

CIRCULATING PULMONARY HYPERTENSION BIOMARKER

CROSS-REFERENCE TO RELATED APPLICATIONS

This application is a 35 U.S.C. § 371 U.S. national entry of International Application PCT/US2015/046251, having an international filing date of Aug. 21, 2015, which claims the benefit of U.S. Provisional Application No. 62/040,266, filed Aug. 21, 2014, the content of each of the aforementioned applications is herein incorporated by reference in their entirety.

FEDERALLY SPONSORED RESEARCH OR DEVELOPMENT

This invention was made with government support under 1RC1HL099786-01 awarded by the National Institutes of Health (NIH). The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "P13104-03_ST25.txt." The sequence listing is 356 bytes in size, and was created on Nov. 25, 2019. It is hereby incorporated by reference in its entirety.

BACKGROUND

Pulmonary artery hypertension (PAH) in children or adults is a progressive and fatal disease with a 3 year survival of 58%. PAH is characterized by sustained elevations of pulmonary artery pressure. Associated pulmonary artery hypertension (APAH) is PAH, which is associated with an underlying pulmonary, cardiac, or systemic disease. Idiopathic pulmonary arterial hypertension (IPAH) is a form of PAH that is present in the absence of an identifiable cause or associated underlying disease. Although advances in therapy and survival with PAH have been made, the etiology is still largely unknown.

In terms of diagnostic or prognostic methods for PAH, clinical functional assessment, such as the 6-minute walk, a test that measures the distance that a patient can walk on a flat, hard surface in a period of 6 minutes, is not applicable to children. In addition, specific diagnostic or prognostic biomarkers are lacking.

Vasodilators are the mainstay of PAH therapy. 20-30% of patients, however, do not respond to vasodilators. Non-responders have a poor prognosis and eventually require lung transplantation. Because the pathobiology is unknown, vasodilator therapy has significant morbidity and cost (~$50,000/year). Further, the diagnostic or prognostic methods to easily and accurately identify patients that are unresponsive to therapy are lacking.

SUMMARY

In some aspects, the presently disclosed subject matter provides methods for predicting or diagnosing pulmonary artery hypertension (PAH), or determining if the therapy used to treat PAH is effective, in infant, children, and adult subjects.

In other aspects, the presently disclosed subject matter provides a method for predicting or diagnosing pulmonary artery hypertension (PAH) in a subject having PAH, at risk of having PAH, or suspected of having PAH, the method comprising: (a) obtaining a sample from a subject at risk of having or suspected of having PAH; (b) detecting a level of expression of at least one biomarker in the sample, wherein the at least one biomarker comprises Hepatoma Derived Growth Factor (HDGF); and (c) comparing the levels of the at least one biomarker in the sample to the levels of the at least one biomarker in a control sample from a subject or subjects that do not have PAH; wherein a significant difference between the levels of the at least one biomarker in the sample and the levels of the at least one biomarker in the control sample is indicative that the subject has or is susceptible to developing PAH. In another aspect, the at least one biomarker comprises HDGF in combination with one or more additional biomarkers selected from the group consisting of Immunoreactive Amino-Terminal Pro-Brain Natriuretic Peptide (NT-PROBNP), Protein S100-A8, Protein S100-A9, Alpha-1B-glycoprotein (A1BG), Beta-2-microglobulin (B2M), Calponin-1 (CNN1), Carbonic anhydrase (CA3), (Complement C4-A (C4A), Tenascin-X (TNXB), Pulmonary surfactant-associated protein C (SFTPC), Uteroglobin (SCGB1A1), Periostin (POSTN), Apolipoprotein A-II (APOA2), Collagen alpha-1(XIV) chain (COL14A1), Complement C3 (C3), Apolipoprotein A-1 (APOA1), Antithrombin-III (SERPINC1), von Willebrand factor (VWF), High mobility group protein B1 (HMGB1), Flavin reductase (NADPH) (BLVRB), Fibulin-1 (FBLN1), Heat shock protein beta-6 (HSPB6), BTB/POZ domain-containing protein (KCTD12), Zyxin (ZYX), Carbonic anhydrase 1 (CA1), Alcohol dehydrogenase 1B (ADH1B), Fibulin-5 (FBLN5), Neutrophil gelatinase-associated lipocalin (LCN2), Serpin H1 (SERPINH1), Periaxin (PRX), Protein S100-A12 (S100A12), Myeloblastin (PRTN3), Alpha-2-macroglobulin (A2M), Serotransferrin (TF), Histone H2B type 1 (HIST1H2BK), Isoform 2 of collagen alpha-1(XVIII) chain (COL18A1), Basement membrane-specific heparin sulfate proteoglycan core protein (HSPG2), Fibrillin-1 (FBN1), Bone marrow stromal antigen 2 (BST2), Matrix metalloproteinase-9 (MMP9), Periplakin (PPL), Serum amyloid A-1 (SAA1), Thrombospondin-1 (THBS1), Tubulin-specific chaperone A (TBCA), Serine-tRNA ligase, cytoplasmic (SARS), and Aldose reductase (AKR1B1).

In further aspects, the presently disclosed subject matter provides a method for determining the efficacy of PAH therapy, e.g., a vasodilator therapy, in a subject undergoing treatment thereof, the method comprising: (a) obtaining a sample from the subject undergoing PAH therapy; (b) detecting a level of expression of at least one biomarker in the sample, wherein the at least one biomarker comprises Hepatoma Derived Growth Factor (HDGF); and (c) comparing the levels of the at least one biomarker in the sample from the subject undergoing PAH therapy to the levels of the at least one biomarker in a previous sample from the subject, wherein a significant difference in the levels of the at least one biomarker in the sample from the subject undergoing PAH therapy as compared to the levels of the at least one biomarker in the previous sample is indicative that the PAH therapy is effective. In another aspect, the at least one biomarker comprises HDGF in combination with one or more additional biomarkers selected from the group consisting of Immunoreactive Amino-Terminal Pro-Brain Natriuretic Peptide (NT-PROBNP), Protein S100-A8, Protein S100-A9, Alpha-1B-glycoprotein (A1BG), Beta-2-microglobulin (B2M), Calponin-1 (CNN1), Carbonic anhydrase (CA3), (Complement C4-A (C4A), Tenascin-X (TNXB), Pulmonary surfactant-associated protein C (SFTPC), Uteroglobin (SCGB1A1), Periostin (POSTN), Apolipoprotein A-II (APOA2), Collagen alpha-1(XIV) chain (COL14A1), Complement C3 (C3), Apolipoprotein A-1 (APOA1), Antithrombin-III (SERPINC1), von Willebrand factor (VWF), High mobility group protein B1 (HMGB1), Flavin reductase (NADPH) (BLVRB), Fibulin-1 (FBLN1), Heat shock protein beta-6 (HSPB6), BTB/POZ domain-containing protein (KCTD12), Zyxin (ZYX), Carbonic anhydrase 1 (CA1), Alcohol dehydrogenase 1B (ADH1B), Fibulin-5 (FBLN5), Neutrophil gelatinase-associated lipocalin (LCN2), Serpin H1 (SERPINH1), Periaxin (PRX), Protein S100-A12 (S100A12), Myeloblastin (PRTN3), Alpha-2-macroglobulin (A2M), Serotransferrin (TF), Histone H2B type 1 (HIST1H2BK), Isoform 2 of collagen alpha-1(XVIII) chain (COL18A1), Basement membrane-specific heparin sulfate proteoglycan core protein (HSPG2), Fibrillin-1 (FBN1), Bone marrow stromal antigen 2 (BST2), Matrix metalloproteinase-9 (MMP9), Periplakin (PPL), Serum amyloid A-1 (SAA1), Thrombospondin-1 (THBS1), Tubulin-specific chaperone A (TBCA), Serine-tRNA ligase, cytoplasmic (SARS), and Aldose reductase (AKR1B1).

In some aspects, the presently disclosed subject matter provides a method for screening for a new PAH therapy, the method comprising: (a) administering a new therapy to a subject known to have PAH; (b) obtaining a sample from the subject; (c) detecting a level of expression of at least one biomarker in the sample, wherein the at least one biomarker comprises Hepatoma Derived Growth Factor (HDGF); and (d) comparing the levels of the at least one biomarker in a sample from a subject known to have PAH to the levels of the at least one biomarker in a control sample from a subject or subjects that do not have PAH or to a previous sample from the subject administered the new therapy; wherein a significant difference between the levels of the at least one biomarker in the sample and levels of the at least one biomarker in the control sample or the previous sample from the subject administered the new therapy is indicative that the new PAH therapy is effective. In another aspect, the at least one biomarker comprises HDGF in combination with one or more additional biomarkers selected from the group consisting of Immunoreactive Amino-Terminal Pro-Brain Natriuretic Peptide (NT-PROBNP), Protein S100-A8, Protein S100-A9, Alpha-1B-glycoprotein (A1BG), Beta-2-microglobulin (B2M), Calponin-1 (CNN1), Carbonic anhydrase (CA3), (Complement C4-A (C4A), Tenascin-X (TNXB), Pulmonary surfactant-associated protein C (SFTPC), Uteroglobin (SCGB1A1), Periostin (POSTN), Apolipoprotein A-II (APOA2), Collagen alpha-1(XIV) chain (COL14A1), Complement C3 (C3), Apolipoprotein A-1 (APOA1), Antithrombin-III (SERPINC1), von Willebrand factor (VWF), High mobility group protein B1 (HMGB1), Flavin reductase (NADPH) (BLVRB), Fibulin-1 (FBLN1), Heat shock protein beta-6 (HSPB6), BTB/POZ domain-containing protein (KCTD12), Zyxin (ZYX), Carbonic anhydrase 1 (CA1), Alcohol dehydrogenase 1B (ADH1B), Fibulin-5 (FBLN5), Neutrophil gelatinase-associated lipocalin (LCN2), Serpin H1 (SERPINH1), Periaxin (PRX), Protein S100-A12 (S100A12), Myeloblastin (PRTN3), Alpha-2-macroglobulin (A2M), Serotransferrin (TF), Histone H2B type 1 (HIST1H2BK), Isoform 2 of collagen alpha-1(XVIII) chain (COL18A1), Basement membrane-specific heparin sulfate proteoglycan core protein (HSPG2), Fibrillin-1 (FBN1), Bone marrow stromal antigen 2 (BST2), Matrix metalloproteinase-9 (MMP9), Periplakin (PPL), Serum amyloid A-1 (SAA1), Thrombospondin-1 (THBS1), Tubulin-specific chaperone A (TBCA), Serine-tRNA ligase, cytoplasmic (SARS), and Aldose reductase (AKR1B1).

In further aspects, the presently disclosed subject matter provides a method for monitoring the progression of pulmonary artery hypertension (PAH) in a subject having PAH, the method comprising: (a) obtaining two or more samples at different time points from a subject having PAH; (b) detecting a level of expression of at least one biomarker in the two or more samples, wherein the at least one biomarker comprises Hepatoma Derived Growth Factor (HDGF); and (c) comparing the levels of the at least one biomarker in the two or more samples to the levels of the at least one biomarker in control samples from a subject or subjects that do not have PAH; wherein a significant difference between the levels of the at least one biomarker in the two or more samples and the levels of the at least one biomarker in the control samples are indicative of PAH progression in the subject.

In other aspects, the methods of the presently disclosed subject matter comprise detecting the level of expression of at least one biomarker by using an enzyme-linked immunosorbent assay (ELISA) method, particularly wherein the at least one biomarker comprises Hepatoma Derived Growth Factor (HDGF). In a particular aspect, the ELISA method comprises: obtaining isolated polyclonal antibodies specific for the amino acid sequence AKEEAEAPGVRDHESL (SEQ ID NO:1); selecting a first polyclonal antibody from said group and attaching said polyclonal antibody to a solid support; reacting a sample suspected of containing HDGF with the isolated polyclonal antibody; selecting a second polyclonal detector antibody selected as recognizing an amino acid sequence which is separate and distinct from the amino acid sequence recognized by the first polyclonal antibody; effecting an immunoreaction; and detecting the immunoreaction.

In still other aspects, the methods of the presently disclosed subject matter further comprise methods of treatment. In further aspects, the methods of treatment comprise informing the patient or a treating physician of the susceptibility of the patient to PAH. In still further aspects, the methods of treatment further comprise a step of administering a therapeutically effective amount of a PAH therapeutic agent, e.g., a vasodilator, to the subject having PAH.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
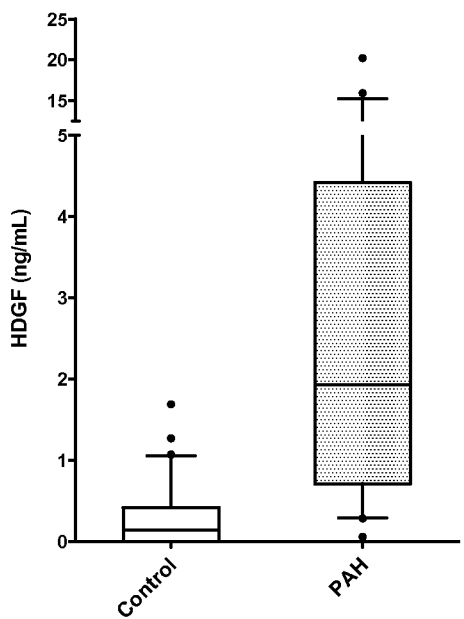
Figure 1B:
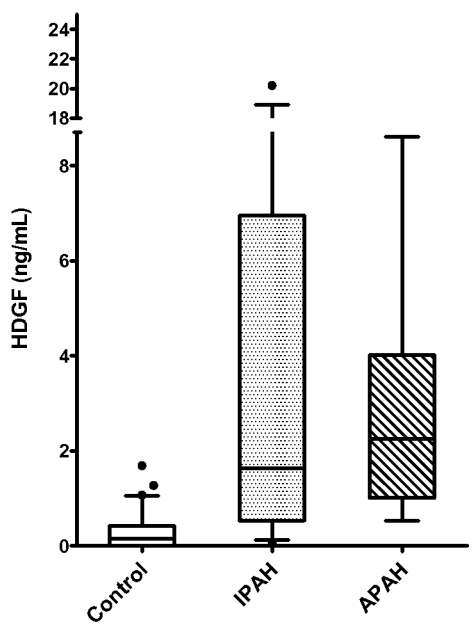
Figure 2A:
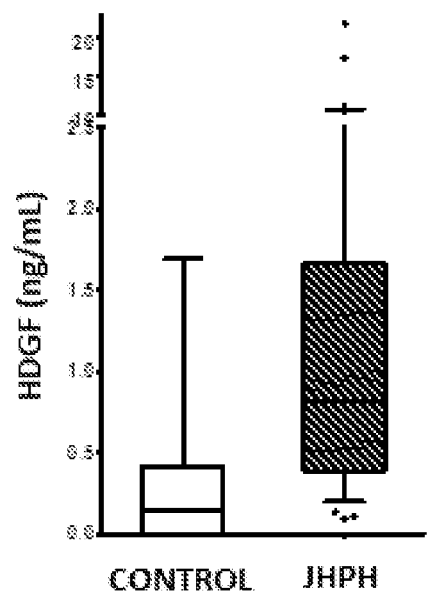
Figure 2B:
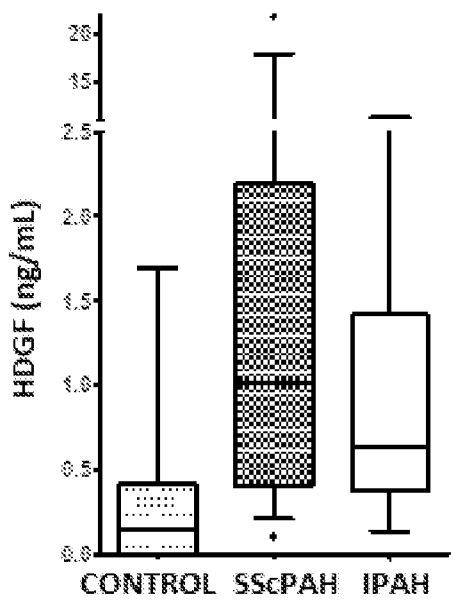
Figure 3:
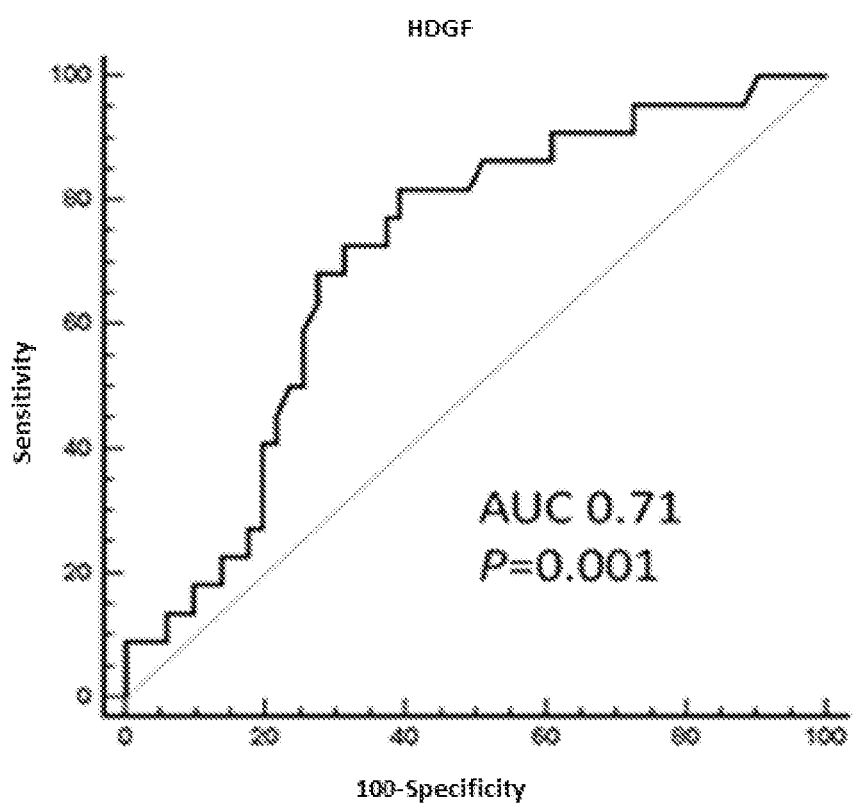
Figure 4:
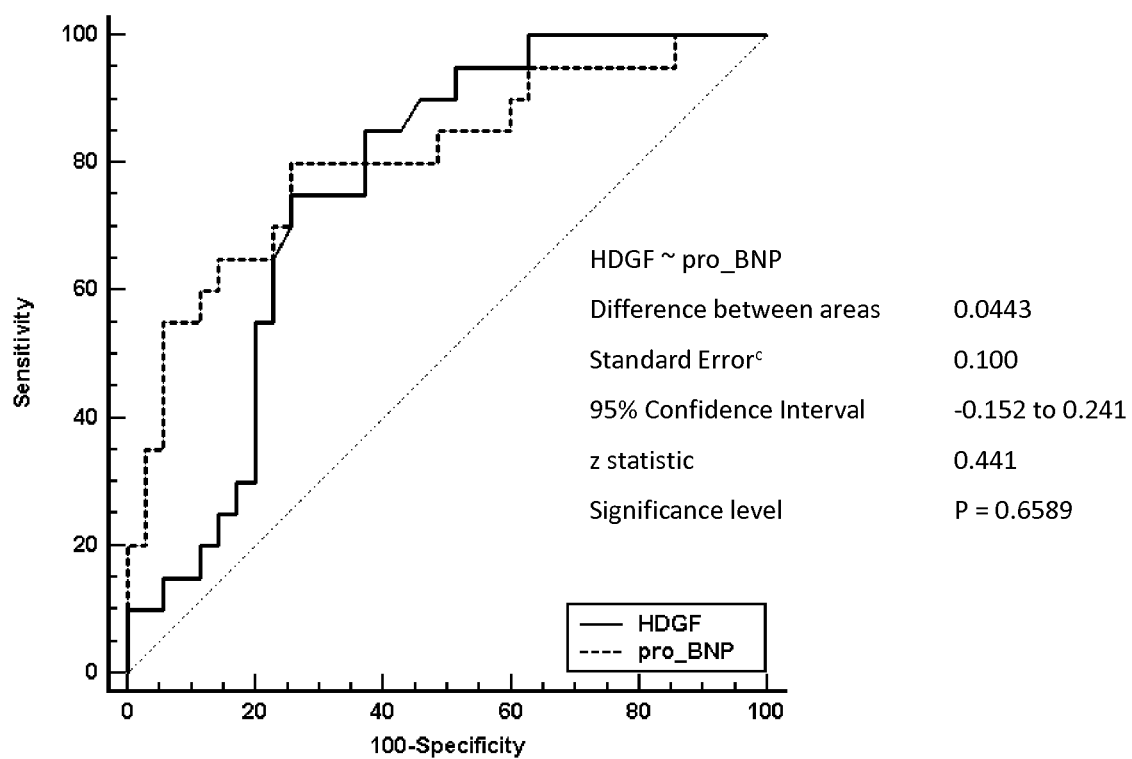
Figure 5:
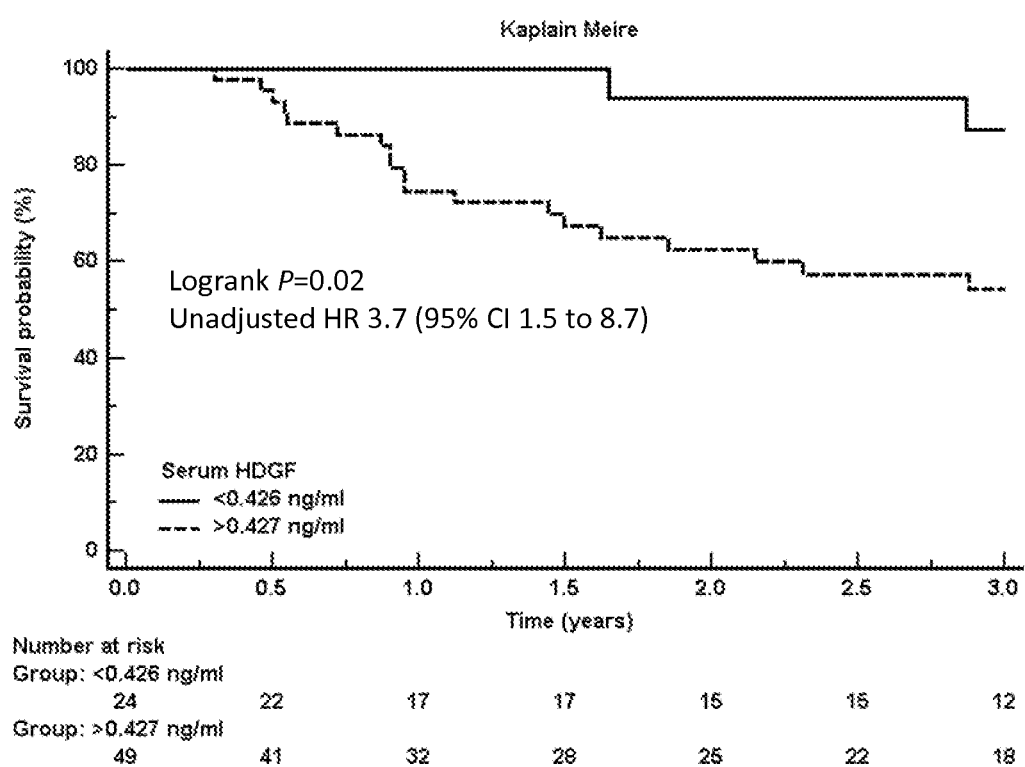
Figure 6:
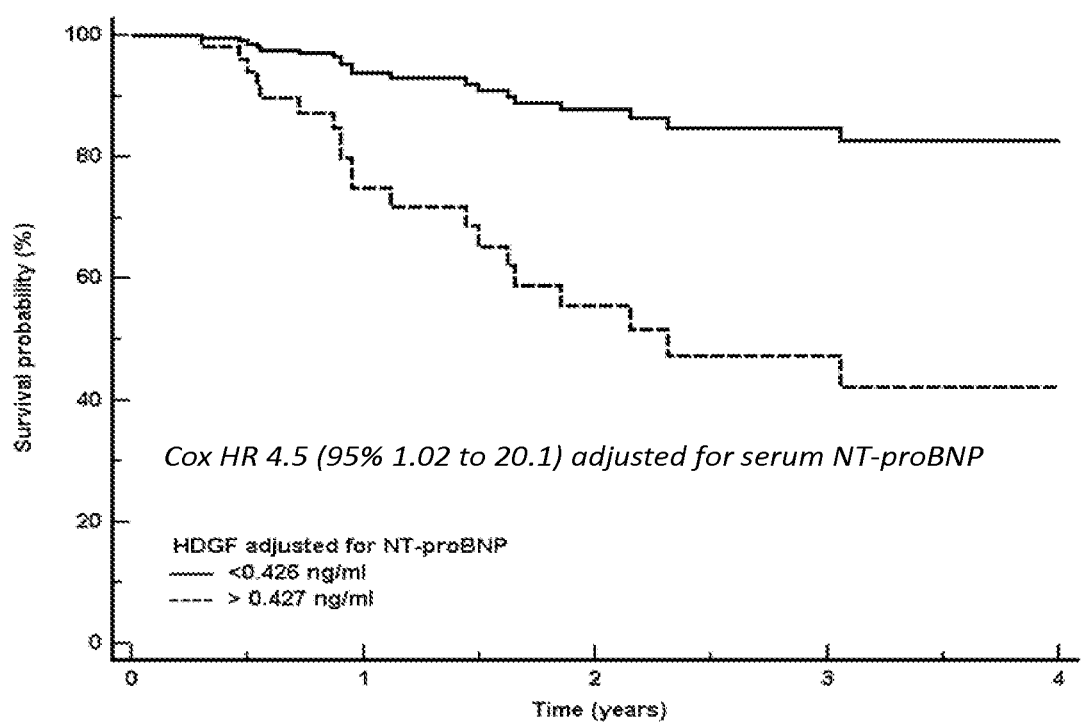
Figure 7A:
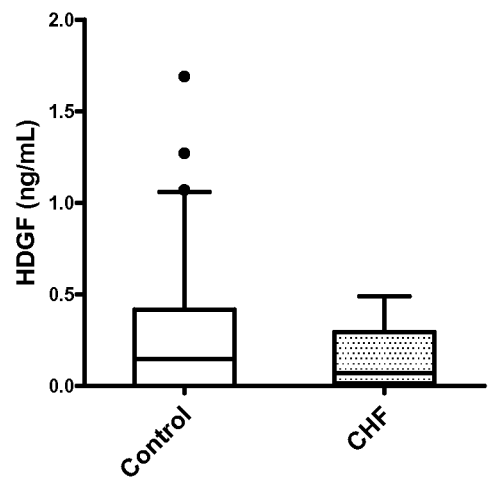
Figure 7B:
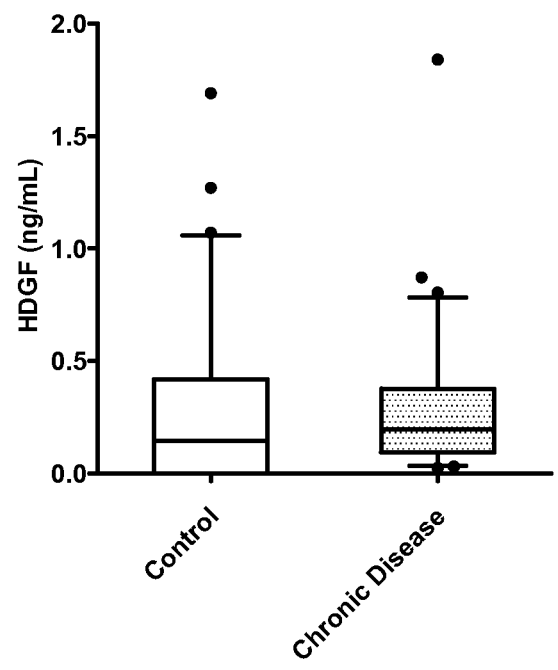
Figure 8:
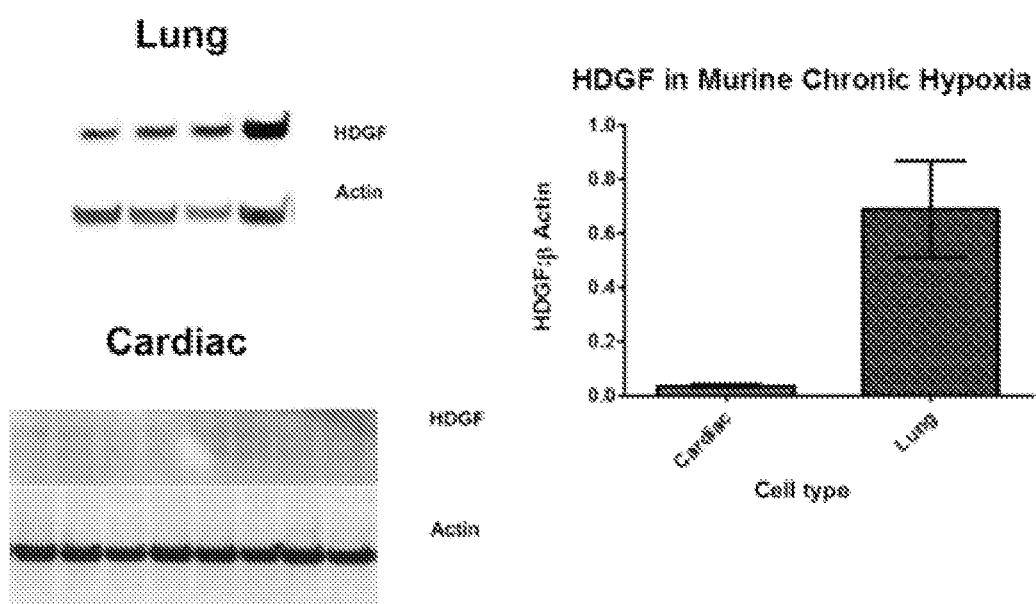

Having thus described the presently disclosed subject matter in general terms, reference will now be made to the accompanying Figures, which are not necessarily drawn to scale, and wherein:

FIG. 1A and FIG. 1B show plasma ELISA verification of HDGF as a pulmonary hypertension biomarker. Using serum samples from the PHBI, Box and whisker plot of serum HDGF levels in PHBI PAH patients in aggregate (FIG. 1A), or subgroups of IPAH and APAH-CHD (B) versus healthy control. Boxes represent the interquartile range (IQR 5-95%) and the horizontal lines are the medians. Outliers are indicated with solid dots. As shown in FIG. 1A, using a new ELISA developed in the laboratory, in aggregate median plasma HDGF levels were approximately 40 fold higher in PAH than normal controls (*=P<0.0001). FIG. 1B shows that both IPAH and APAH-CHD groups were significantly increased compared to healthy controls (P<0.0001), demonstrating that HDGF elevation in PAH is not PAH subtype specific;

FIG. 2A and FIG. 2B show that in a second validation cohort from the Johns Hopkins Pulmonary Hypertension Clinic that serum HDGF levels in patients with PAH vs healthy control (p=0.0003) or subgroups of SSc-PAH (p=0.0001) and IPAH (p=0.0005) verses healthy control are significantly increased. Boxes represent the interquartile range (IQR 5-95%) and the horizontal lines are the medians;

FIG. 3 shows HDGF serum concentrations ROC curve demonstrating significant prediction of survival in PAH;

FIG. 4 shows that HDGF and NT-proBNP ROC curves are not different for predicting PAH survival;

FIG. 5 shows that HDGF serum concentration is a significant predictor of PAH survival. A serum HDGF level>0.426 has a Cox HR of 3.7;

FIG. 6 shows that HDGF adjusted for NT-proBNP is an even greater predictor of PAH survival (Cox HR 4.5), indicating that NT-proBNP and HDGF levels represent different pathobiology processes in PAH;

FIG. 7A and FIG. 7B show that serum HDGF level was measured by ELISA is specific for pulmonary hypertension as not elevated in patients with left sided heart failure or chronic disease. FIG. 7A shows that serum HDGF level in chronic heart failure cohort (median 0.07 ng/mL, n=17) vs healthy control (median 0.145 ng/mL, n=60, P=0.162) was not significant. FIG. 7B shows that serum HDGF levels were also not significantly different (p=0.906) in a chronic disease cohort (median 0.195 ng/mL, n=66, smoking, hypertension, diabetes and obesity) vs healthy controls (median 0.145 ng/mL, n=60); and FIG. 8 shows that HDGF is highly expressed in the lung but not in the heart using the hypoxia mouse model of pulmonary hypertension. HDGF protein level in mouse lung and cardiac tissue were assessed by Western blotting using polyclonal anti HDGF antibody on mouse lung and left heart tissue lysate. Lung, heart, and HDGF protein level plot, are shown (the protein level was analyzed using ImageJ and normalized by actin), demonstrating that with pulmonary hypertension, unlike BNP, the heart is not the major source for circulating HDGF.

DETAILED DESCRIPTION

The presently disclosed subject matter now will be described more fully hereinafter with reference to the accompanying Figures, in which some, but not all aspects of the presently disclosed subject matter are shown. Like numbers refer to like elements throughout. The presently disclosed subject matter may be embodied in many different forms and should not be construed as limited to the aspects set forth herein; rather, these aspects are provided so that this disclosure will satisfy applicable legal requirements. Indeed, many modifications and other aspects of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific aspects disclosed and that modifications and other aspects are intended to be included within the scope of the appended claims.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning. A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml.

Pulmonary artery hypertension (PAH) in children or adults is a progressive and fatal disease characterized by sustained elevations of pulmonary artery pressure. Diagnostic or prognostic methods to easily and accurately identify patients who are at risk for PAH are lacking. In addition, diagnostic or prognostic methods to identify patients unresponsive to vasodilator therapy, the main therapy used for PAH patients, or other drug therapies, are also lacking.

As further described below, the presently disclosed subject matter relates to the discovery that Hepatoma Derived Growth Factor (HDGF) is a significant PAH diagnostic and prognostic biomarker and is at least equivalent to the current standard of care PAH biomarker Immunoreactive Amino-Terminal Pro-Brain Natriuretic Peptide (NT-PROBNP) for predicting PAH survival. HDGF is a nuclear targeted SMC and pulmonary endothelial cell expressed mitogen (Everett et al. (2000) *J. Clin. Invest.* 105:567-575; Everett et al. (2001) *J. Biol. Chem.* 276:37564-37568; Everett et al. (2004) *Am. J. Physiol. Lung* 286:L1194-1201; Ren et al. (2004) *J. Clin. Oncol.* 22:3230-7; Okuda et al. (2005) *Cancer Science* 94:1034-1041; Narron et al. (2006) *Peds. Res.* 59:778-783; Zhanga et al. (2010) *J. Immunological Methods* 355:61-67). HDGF has also been shown to play a role in the pathogenesis of lung cancer (Ren et al. (2004) *J. Clin. Oncol.* 22:3230-7).

Accordingly, in some aspects, the presently disclosed subject matter provides a method for predicting or diagnosing pulmonary artery hypertension (PAH) in a subject having PAH, at risk of having PAH, or suspected of having PAH.

In another aspect, the presently disclosed subject matter provides a method for determining the efficacy of PAH therapy, e.g., a vasodilator therapy, in a subject undergoing treatment thereof. In a further aspect, the methods of the presently disclosed subject matter further comprise methods of treatment comprising informing the patient or a treating physician of the susceptibility of the patient to PAH and/or a step of administering a therapeutically effective amount of a PAH therapeutic agent, e.g., a vasodilator, to the subject having PAH. The diagnostic markers, prognostic markers, or therapeutic efficacy markers of the presently disclosed methods can be used for the in vivo assessment of pulmonary hypertension in a patient. For example, the presently disclosed methods can be used in critically ill patients where standard non-invasive echocardiograpy imaging and Doppler assessment are non-diagnostic and/or not quantifiable. Another example is the development of pulmonary hypertension as a consequence of worsening left heart failure. The presently disclosed methods also provide a way to intervene before overt PAH occurs, decrease therapeutic morbidity, and appropriately titrate therapy.

The presently disclosed subject matter allows in vivo assessment of pulmonary hypertension of all etiologies and in patients of all ages. In some aspects, the methods allow a diagnosis of a range or extent of PAH in a patient. The patient may be an infant, a child, or an adult. In some aspects, the patient is already presenting symptoms of PAH (overt). In other aspects, the patient does not show any signs of having or likely to develop PAH (subclinical). It is expected that earlier diagnosis and intervention in a patient, such as an infant or small child, will result in improved outcomes. In further aspects, the methods provided allow the assessment and monitoring of the efficacy of pulmonary hypertension therapies in infants, children, and adults.

In other aspects, the presently disclosed subject matter provides a method for screening for a new PAH therapy. For example, the presently disclosed methods can be used to screen and compare treatment protocols or therapeutic drugs and their combinations. The presently disclosed methods also may be directly applied to cell culture or animal models of pulmonary hypertension as a research tool.

In still other aspects, the methods of the presently disclosed subject matter comprise detecting the level of expression of at least one biomarker by using an enzyme-linked immunosorbent assay (ELISA) method.

I. Methods for Predicting or Diagnosing Pulmonary Artery Hypertension

In some aspects, the presently disclosed subject matter provides a method for predicting or diagnosing pulmonary artery hypertension (PAH) in a subject having PAH, at risk of having PAH, or suspected of having PAH, the method comprising: (a) obtaining a sample from a subject at risk of having or suspected of having PAH; (b) detecting a level of expression of at least one biomarker in the sample, wherein the at least one biomarker comprises Hepatoma Derived Growth Factor (HDGF); and (c) comparing the levels of the at least one biomarker in the sample to the levels of the at least one biomarker in a control sample from a subject or subjects that do not have PAH; wherein a significant difference between the levels of the at least one biomarker in the sample and the levels of the at least one biomarker in the control sample is indicative that the subject has or is susceptible to developing PAH.

In another aspect, the at least one biomarker within the methods for predicting or diagnosing pulmonary artery hypertension (PAH) in a subject having PAH, at risk of having PAH, or suspected of having PAH comprises HDGF in combination with one or more additional biomarkers selected from the group consisting of Immunoreactive Amino-Terminal Pro-Brain Natriuretic Peptide (NT-PROBNP), Protein S100-A8, Protein S100-A9, Alpha-1B-glycoprotein (A1BG), Beta-2-microglobulin (B2M), Calponin-1 (CNN1), Carbonic anhydrase (CA3), (Complement C4-A (C4A), Tenascin-X (TNXB), Pulmonary surfactant-associated protein C (SFTPC), Uteroglobin (SCGB1A1), Periostin (POSTN), Apolipoprotein A-II (APOA2), Collagen alpha-1(XIV) chain (COL14A1), Complement C3 (C3), Apolipoprotein A-1 (APOA1), Antithrombin-III (SERPINC1), von Willebrand factor (VWF), High mobility group protein B1 (HMGB1), Flavin reductase (NADPH) (BLVRB), Fibulin-1 (FBLN1), Heat shock protein beta-6 (HSPB6), BTB/POZ domain-containing protein (KCTD12), Zyxin (ZYX), Carbonic anhydrase 1 (CA1), Alcohol dehydrogenase 1B (ADH1B), Fibulin-5 (FBLN5), Neutrophil gelatinase-associated lipocalin (LCN2), Serpin H1 (SERPINH1), Periaxin (PRX), Protein S100-A12 (S100A12), Myeloblastin (PRTN3), Alpha-2-macroglobulin (A2M), Serotransferrin (TF), Histone H2B type 1 (HIST1H2BK), Isoform 2 of collagen alpha-1(XVIII) chain (COL18A1), Basement membrane-specific heparin sulfate proteoglycan core protein (HSPG2), Fibrillin-1 (FBN1), Bone marrow stromal antigen 2 (BST2), Matrix metalloproteinase-9 (MMP9), Periplakin (PPL), Serum amyloid A-1 (SAA1), Thrombospondin-1 (THBS1), Tubulin-specific chaperone A (TBCA), Serine-tRNA ligase, cytoplasmic (SARS), and Aldose reductase (AKR1B1).

As used herein, the term "sample" refers to any sampling of cells, tissues, or bodily fluids in which expression of a biomarker can be detected. The sample may be a part of a subject in vivo or ex vivo. For example, a sample may be blood, serum, plasma, urine, saliva, tissue, lung, lymph or any other part of a subject that can be removed.

As used herein, the term "control sample", "corresponding control", or "appropriate control" means any control or standard familiar to one of ordinary skill in the art useful for comparison purposes. For example, the control sample may be taken from a subject or subjects that do not have a specific disease, disorder, or condition, such as PAH.

As used herein, a "biomarker" is any gene or protein whose level of expression in a cell or tissue is altered in some way compared to that of a normal or healthy cell or tissue. In some aspects, the amount of biomarker may be changed. In other aspects, the biomarker may be differentially modified in some way. Biomarkers of the presently disclosed subject matter are selective for PAH. In some cases, proteins are listed as biomarkers but it is understood that the proteins themselves do not need to be detected but nucleic acids correlating to the proteins can be detected instead in the methods of the presently disclosed subject matter.

As used herein, the terms "measuring" and "determining" refer to methods which include detecting the level of a biomarker(s) in a sample.

The methods of the presently disclosed subject matter comprise the detection of specific biomarkers with changes in levels of expression in subjects having PAH. The change in levels of biomarker may be an increase or decrease, depending on the biomarker(s) being assayed. In some aspects, at least one biomarker comprising Hepatoma Derived Growth Factor (HDGF) and one or more biomarker found in the lung or circulating in patients suspected of having PAH can be measured and compared to controls to determine whether the patient is likely to get or already has PAH. It is expected that in some aspects, combinations of disclosed biomarker panels will improve sensitivity and/or specificity of the methods.

The levels of biomarkers observed using the presently disclosed methods are significantly different in a patient or subject having PAH, at risk of having PAH, or suspected of having PAH as compared to the levels of biomarker found in a control subject not having PAH. In some aspects, the levels of biomarker found in a subject having PAH, at risk of having PAH, or suspected of having PAH are higher than the levels in a control subject, and in other aspects, the levels are lower. The biomarkers may be found anywhere in the body of a patient, such as the lung, plasma, serum, blood, lymph, saliva and urine. In some aspects, the sample is selected from the group consisting of lung tissue, blood, plasma, saliva, urine, and serum. As used herein, the terms "significantly different" or "significant difference" mean a level of expression of a biomarker in a sample that is higher or lower than the level of expression of said biomarker in a control sample by at least 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 3.6 fold, 3.7 fold, 3.8 fold, 3.9 fold, 4.0 fold, 4.1 fold, 4.2 fold, 4.3 fold, 4.4 fold, 4.5 fold, 4.6 fold, 4.7 fold, 4.8 fold, 4.9 fold, 5.0 fold or more.

As used herein, the term "comparing" refers to making an assessment of how the proportion, level or cellular localization of one or more biomarkers is a sample from a patient relates to the proportion, level or cellular localization of one or more biomarkers in a control sample. For example, "comparing" may refer to assessing whether the proportion, level or cellular localization of one or more biomarkers in a sample from a patient is the same as, more or less than, or different in proportion, level, or cellular localization of the corresponding one or more biomarkers in a standard or control sample. More particularly, the term may refer to assessing whether the proportion, level, or cellular localization of one or more biomarkers in a patient is the same as, more or less than, different from or otherwise corresponds to the proportion, level, or cellular localization of predefined biomarker levels that correspond to, for example, a patient having PAH, not having PAH, responding to treatment for PAH, not responding to treatment for PAH, likely or not likely to respond to a particular PAH treatment, or having/not having another disease or condition.

As used herein, the term "level of expression" of a biomarker refers to the amount of biomarker detected. Levels of biomarker can be detected at the transcriptional level, the translational level, and the post-translational level, for example.

As used herein, the term "subject at risk" of getting a disease refers to estimating that a subject will have a disease or disorder in the future based on the subject's current symptoms, family history, lifestyle choices, and the like.

As used herein, the term "indicative" or "likely" means that the event referred to is probable. For example, if the methods of the presently disclosed subject matter result in a conclusion that the subject is likely to get PAH, that means it is probable that the subject will get PAH.

As used herein, the term "diagnosing" refers to the process of attempting to determine or identify a disease or disorder.

The subject within the presently disclosed methods in their many aspects is desirably a human subject, although it is to be understood that the methods described herein are effective with respect to all vertebrate species, which are intended to be included in the term "subject." Accordingly, a "subject" can include a human subject for medical purposes, such as for treating an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some aspects, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

The presently disclosed methods may be used for any type of PAH, such as idiopathic, newborn, and pulmonary hypertension from other causes, such as structural heart disease, lung disease, inflammatory disease, and heart failure. In some aspects, the type of PAH is selected from the group consisting of idiopathic pulmonary artery hypertension (IPAH), associated pulmonary artery hypertension (APAH), PAH caused by structural heart disease, PAH caused by lung disease, PAH caused by inflammatory disease, PAH caused by heart failure, PAH caused by congenital heart disease, pulmonary hypertension in the newborn and familial pulmonary artery hypertension (FPAH) arising from de novo or inherited gene defects.

Any methods available in the art for identifying or detecting the presently disclosed biomarkers are encompassed herein. For example, the overexpression or underexpression of a biomarker can be detected on a nucleic acid level or a protein level. Nucleic acid-based techniques for assessing expression are well known in the art and include, for example, determining the level of biomarker mRNA in a sample. Isolated mRNA can be used in hybridization or amplification assays that include, but are not limited to, Southern or Northern analyses, polymerase chain reaction analyses and probe arrays.

In some aspects, the levels of protein are detected. In particular aspects, the biomarkers of the presently disclosed subject matter can be detected and/or measured by immunoassay Immunoassays require biospecific capture reagents, such as antibodies to capture the biomarker. In some aspects, the immunoassay comprises an antibody. Many antibodies are available commercially and in addition, antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art.

As used herein, the term "antibody" is used in the broadest sense and encompasses naturally occurring forms of antibodies and recombinant antibodies such as single-chain antibodies, chimeric and humanized antibodies and multi-specific antibodies as well as fragments and derivatives of all of the foregoing.

The presently disclosed subject matter includes immunoassays, including but not limited to, sandwich immunoassays including ELISA or fluorescence-based immunoassays, immunoblots, Western blots, immunoprecipitation, immunofluorescence, and immunocytochemistry. Nephelometry is an assay performed in liquid phase, in which antibodies are in solution. Binding of an antigen to an antibody results in changes in absorbance, which is then measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry. In addition to antibodies, the presently disclosed subject matter includes any other suitable agent (e.g., a peptide, an aptamer, or a small organic molecule) that specifically binds a disclosed biomarker.

The levels of protein may also be detected by mass spectroscopy, a method that employs a mass spectrometer. Examples of mass spectrometers include time-of-flight, magnetic sector, quadrupole filter, ion trap, ion cyclotron resonance, electrostatic sector analyzer, hybrids or combinations of the foregoing, and the like. In other aspects, the mass spectrometric method comprises matrix assisted laser desorption/ionization time-of-flight (MALDI-TOF MS or MALDI-TOF). In some other aspects, the method comprises MALDI-TOF tandem mass spectrometry (MALDI-TOF MS/MS). In yet another aspect, mass spectrometry can be combined with another appropriate method(s) as may be contemplated by one of ordinary skill in the art. For example, MALDI-TOF can be combined with trypsin digestion and tandem mass spectrometry as described herein. In particular aspects, the mass spectrometric method comprises selected reaction monitoring (SRM) or multiple reaction monitoring (MRM), which are highly specific and sensitive mass spectrometry techniques that can selectively quantify compounds within complex mixtures.

The biomarkers of the presently disclosed subject matter may also be detected by other suitable methods. These methods include, but are not limited to, optical methods, biochips, electrochemical methods (voltametry and amperometry techniques), atomic force microscopy, and radio frequency methods, e.g., multipolar resonance spectroscopy. Optical methods include but are not limited to microscopy (both confocal and non-confocal), detection of fluorescence, luminescence, chemiluminescence, absorbance, reflectance, transmittance, and birefringence or refractive index (e.g., surface Plasmon resonance, ellipsometry, a resonant mirror method, a grating coupler waveguide method or interferometry). Biochips generally comprise solid substrates and have a generally planar surface, to which a capture reagent (also called an adsorbent or affinity reagent) is attached. Protein biochips are biochips adapted for the capture of polypeptides. Many protein biochips are described in the art. Another detection method includes an electrochemicaluminescent assay, which uses labels that emit light when electrochemically stimulated.

In some aspects, a combination of biomarkers is detected. By "combination" it is meant that at least two biomarkers of the presently disclosed subject matter are detected and at least two biomarker levels of expression are compared to the levels of biomarkers in a control sample, wherein at least one biomarker comprises Hepatoma Derived Growth Factor (HDGF). Accordingly, at least 2, 3, 4, 5, 6, 7, 8, 9, 10 or more biomarkers may be used in a panel of biomarkers in the methods of the presently disclosed subject matter. In some cases, a more accurate determination of PAH can be made by using more than one biomarker.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. A ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative. Diagnostic tests that use these biomarkers may show a ROC of at least about 0.6, at least about 0.7, at least about 0.8, or at least about 0.9.

The biomarkers are differentially present in subjects with PAH and subjects without PAH, and therefore, are useful in aiding in the determination of whether a subject has or is at risk of having PAH. In certain aspects, the biomarkers are measured in a patient sample using the methods described herein and compared, for example, to predefined biomarker levels and correlated to PAH status. In particular aspects, the measurement(s) may then be compared with a relevant diagnostic amount(s), cut-off(s), or multivariate model scores that distinguish a positive PAH status from a negative PAH status. The diagnostic amount(s) represents a measured amount of a biomarker(s) above which or below which a patient is classified as having a particular PAH status. For example, if the biomarker(s) is/are up-regulated compared to normal levels in a patient that has PAH, then a measured amount above the diagnostic cut-off(s) provides a diagnosis of PAH. Alternatively, if the biomarker(s) is/are down-regulated compared to normal levels in a patient that has PAH, then a measured amount at or below the diagnostic cut-off(s) provides a diagnosis of PAH. As is well understood in the art, by adjusting the particular diagnostic cut-off(s) used in an assay, one can increase the sensitivity or specificity of the diagnostic assay. In particular aspects, the diagnostic cut-off can be determined, for example, by measuring the amount of biomarkers in a statistically significant number of samples from patients with the different PAH statuses, and drawing the cut-off to suit the desired levels of specificity and sensitivity. In some aspects, a positive result is assumed if a sample is positive for at least one of the biomarkers of the presently disclosed subject matter.

Furthermore, in some aspects, the values measured for markers of a biomarker panel are mathematically combined and the combined value is correlated to the underlying diagnostic question. Biomarker values may be combined by any appropriate state of the art mathematical method. In a specific aspect, the presently disclosed subject matter provides methods for determining the risk of developing PAH in a patient. Biomarker percentages, amounts, or patterns are characteristic of various risk states, such as high, medium, or low. The risk of developing PAH is determined by measuring the relevant biomarkers and then either submitting them to a classification algorithm or comparing them with a control or reference amount or sample, i.e., a predefined level or pattern of biomarkers that is associated with the particular risk level.

II. Methods for Monitoring the Progression of Pulmonary Artery Hypertension

In further aspects, the presently disclosed subject matter provides a method for monitoring the progression of pulmonary artery hypertension (PAH) in a subject having PAH, the method comprising: (a) obtaining two or more samples at different time points from a subject having PAH; (b) detecting a level of expression of at least one biomarker in the two or more samples, wherein the at least one biomarker comprises Hepatoma Derived Growth Factor (HDGF); and (c) comparing the levels of the at least one biomarker in the two or more samples to the levels of the at least one biomarker in control samples from a subject or subjects that do not have PAH; wherein a significant difference between the levels of the at least one biomarker in the two or more samples and the levels of the at least one biomarker in the control samples are indicative of PAH progression in the subject.

III. Methods to Determine the Efficacy of Pulmonary Artery Hypertension Therapy PAH therapies include, but are not limited to, vasodilator therapy. Examples of vasodilator therapy drugs include, but are not limited to, phosphodiesterase 5 (PDE5) inhibitors, prostacyclins, and endothelin receptor antagonists. A significant percentage of patients, however, do not respond to vasodilators. Non-responders have a poor prognosis and eventually require lung transplantation to survive. In addition, vasodilator therapy has significant morbidity and cost. No easy and accurate PAH specific way to determine if vasodilator therapy is working in a subject of all ages with PAH is currently available.

Accordingly, the presently disclosed subject matter also provides a method for determining the efficacy of PAH therapy, e.g., a vasodilator therapy, in a subject undergoing treatment thereof, the method comprising: (a) obtaining a sample from the subject undergoing PAH therapy; (b) detecting a level of expression of at least one biomarker in the sample, wherein the at least one biomarker comprises Hepatoma Derived Growth Factor (HDGF); and (c) comparing the levels of the at least one biomarker in the sample from the subject undergoing PAH therapy to the levels of the at least one biomarker in a previous sample from the subject, wherein a significant difference in the levels of the at least one biomarker in the sample from the subject undergoing PAH therapy as compared to the levels of the at least one biomarker in the previous sample is indicative that the PAH therapy is effective.

As used herein, the term "effective" means amelioration of one or more causes or symptoms of a disease or disorder, such as PAH. Such amelioration only requires a reduction or alteration, not necessarily elimination, of said causes or symptoms.

In another aspect, the at least one biomarker within the methods for determining the efficacy of PAH therapy, e.g., a vasodilator therapy, in a subject undergoing treatment thereof comprises HDGF in combination with one or more additional biomarkers selected from the group consisting of Immunoreactive Amino-Terminal Pro-Brain Natriuretic Peptide (NT-PROBNP), Protein S100-A8, Protein S100-A9, Alpha-1B-glycoprotein (A1BG), Beta-2-microglobulin (B2M), Calponin-1 (CNN1), Carbonic anhydrase (CA3), (Complement C4-A (C4A), Tenascin-X (TNXB), Pulmonary surfactant-associated protein C (SFTPC), Uteroglobin (SCGB1A1), Periostin (POSTN), Apolipoprotein A-II (APOA2), Collagen alpha-1(XIV) chain (COL14A1), Complement C3 (C3), Apolipoprotein A-1 (APOA1), Antithrombin-III (SERPINC1), von Willebrand factor (VWF), High mobility group protein B1 (HMGB1), Flavin reductase (NADPH) (BLVRB), Fibulin-1 (FBLN1), Heat shock protein beta-6 (HSPB6), BTB/POZ domain-containing protein (KCTD12), Zyxin (ZYX), Carbonic anhydrase 1 (CA1), Alcohol dehydrogenase 1B (ADH1B), Fibulin-5 (FBLN5), Neutrophil gelatinase-associated lipocalin (LCN2), Serpin H1 (SERPINH1), Periaxin (PRX), Protein S100-A12 (S100A12), Myeloblastin (PRTN3), Alpha-2-macroglobulin (A2M), Serotransferrin (TF), Histone H2B type 1 (HIST1H2BK), Isoform 2 of collagen alpha-1(XVIII) chain (COL18A1), Basement membrane-specific heparin sulfate proteoglycan core protein (HSPG2), Fibrillin-1 (FBN1), Bone marrow stromal antigen 2 (BST2), Matrix metalloproteinase-9 (MMP9), Periplakin (PPL), Serum amyloid A-1 (SAA1), Thrombospondin-1 (THBS1), Tubulin-specific chaperone A (TBCA), Serine-tRNA ligase, cytoplasmic (SARS), and Aldose reductase (AKR1B1).

IV. Methods for Screening for New Therapies for Pulmonary Artery Hypertension The presently disclosed methods can be used to evaluate existing and new therapies in vitro, in vivo, or ex vivo. In some aspects, the methods can be used to screen drugs in cell culture. For example, a cell can be contacted with a potential therapeutic drug and at least one biomarker disclosed herein can be assayed for levels of expression. As another example, PAH can be monitored or researched in an animal model by using the biomarkers disclosed in the methods described herein. In some aspects, the methods can be used to screen for new protocols or drugs in a subject by monitoring the biomarkers disclosed herein.

Accordingly, the presently disclosed subject matter provides a method for screening for a new PAH therapy, the method comprising: (a) administering a new therapy to a subject known to have PAH; (b) obtaining a sample from the subject; (c) detecting a level of expression of at least one biomarker in the sample, wherein the at least one biomarker comprises Hepatoma Derived Growth Factor (HDGF); and (d) comparing the levels of the at least one biomarker in a sample from a subject known to have PAH to the levels of the at least one biomarker in a control sample from a subject or subjects that do not have PAH or to a previous sample from the subject administered the new therapy; wherein a significant difference between the levels of the at least one biomarker in the sample and levels of the at least one biomarker in the control sample or the previous sample from the subject administered the new therapy is indicative that the new PAH therapy is effective.

In another aspect, the at least one biomarker within the methods for screening for a new PAH therapy comprises HDGF in combination with one or more additional biomarkers selected from the group consisting of Immunoreactive Amino-Terminal Pro-Brain Natriuretic Peptide (NT-PROBNP), Protein S100-A8, Protein S100-A9, Alpha-1B-glycoprotein (A1BG), Beta-2-microglobulin (B2M), Calponin-1 (CNN1), Carbonic anhydrase (CA3), (Complement C4-A (C4A), Tenascin-X (TNXB), Pulmonary surfactant-associated protein C (SFTPC), Uteroglobin (SCGB1A1), Periostin (POSTN), Apolipoprotein A-II (APOA2), Collagen alpha-1(XIV) chain (COL14A1), Complement C3 (C3), Apolipoprotein A-1 (APOA1), Antithrombin-III (SERPINC1), von Willebrand factor (VWF), High mobility group protein B1 (HMGB1), Flavin reductase (NADPH) (BLVRB), Fibulin-1 (FBLN1), Heat shock protein beta-6 (HSPB6), BTB/POZ domain-containing protein (KCTD12), Zyxin (ZYX), Carbonic anhydrase 1 (CA1), Alcohol dehydrogenase 1B (ADH1B), Fibulin-5 (FBLN5), Neutrophil gelatinase-associated lipocalin (LCN2), Serpin H1 (SER- PINH1), Periaxin (PRX), Protein S100-A12 (S100A12), Myeloblastin (PRTN3), Alpha-2-macroglobulin (A2M), Serotransferrin (TF), Histone H2B type 1 (HIST1H2BK), Isoform 2 of collagen alpha-1(XVIII) chain (COL18A1), Basement membrane-specific heparin sulfate proteoglycan core protein (HSPG2), Fibrillin-1 (FBN1), Bone marrow stromal antigen 2 (BST2), Matrix metalloproteinase-9 (MMP9), Periplakin (PPL), Serum amyloid A-1 (SAA1), Thrombospondin-1 (THBS1), Tubulin-specific chaperone A (TBCA), Serine-tRNA ligase, cytoplasmic (SARS), and Aldose reductase (AKR1B1).

In other aspects, the new therapy is a drug. In still other aspects, the subject is a human or an animal.

V. ELISA Method for the Detection of a PAH Biomarker

In other aspects, the methods of the presently disclosed subject matter comprise detecting the level of expression of at least one biomarker by using an enzyme-linked immunosorbent assay (ELISA) method, particularly wherein the at least one biomarker comprises Hepatoma Derived Growth Factor (HDGF). In a particular aspect, the ELISA method comprises: obtaining isolated polyclonal antibodies specific for the amino acid sequence AKEEAEAPGVRDHESL (SEQ ID NO:1); selecting a first polyclonal antibody from said group and attaching said polyclonal antibody to a solid support; reacting a sample suspected of containing HDGF with the isolated polyclonal antibody; selecting a second polyclonal detector antibody selected as recognizing an amino acid sequence which is separate and distinct from the amino acid sequence recognized by the first polyclonal antibody; effecting an immunoreaction; and detecting the immunoreaction.

In one non-limiting example, a sandwich ELISA technique may be used to measure circulating HDGF in human plasma. Microplate wells coated with polyclonal anti-HDGF capture protein may constitute the solid phase. Test subject plasma, standards, and controls may be added to the coated wells and incubated with incubation buffer. If HDGF protein is present in the test sample, it will be captured by HDGF specific antibody coated on the wells. After incubation and washing, a biotinylated polyclonal anti-HDGF detector antibody may be added to the wells. The detector antibody binds to the HDGF, or immunogenic fragments thereof, e.g. polypeptide fragments which are recognized by the antibody, which are in turn bound to anti-HDGF capture antibody, thus forming a sandwich. After incubation and washing, a horseradish peroxidase (HRP)-streptavidin conjugate solution may be added to the wells. Following incubation and washing, an enzyme substrate may be added to the wells and incubated. An acidic solution may then be added in order to stop the enzymatic reaction. The degree of enzymatic activity of immobilized HRP may be determined by measuring the optical density of the oxidized enzymatic product in the wells, e.g. at 450 nm. The absorbance is proportional to the amount of HDGF in the test subject sample. A set of HDGF protein standards may be used to generate a standard curve of absorbance versus HDGF concentration from which the HDGF concentrations in test specimens and controls can be calculated. It is understood that detection of the immunoreaction may be accomplished via direct or indirect methods which are well-known in the art.

VI. Diagnostic Kits

The presently disclosed subject matter also relates to kits for practicing the methods of the invention. By "kit" is intended any article of manufacture (e.g., a package or a container) comprising a substrate for collecting a biological sample from the patient and means for measuring the level of at least one biomarker in the sample, wherein the at least one biomarker comprises Hepatoma Derived Growth Factor (HDGF).

Accordingly, in one aspect, the presently disclosed subject matter provides a diagnostic kit for determining predicting or diagnosing pulmonary artery hypertension (PAH) in a subject having PAH, at risk of having PAH, or suspected of having PAH, the kit comprising: (a) a substrate for collecting a biological sample from the patient; and (b) means for measuring the levels of at least one biomarker in the sample, wherein the at least one biomarker comprises Hepatoma Derived Growth Factor (HDGF).

Additional biomarkers for use within the kits of the presently disclosed subject matter may be selected from the group consisting of Immunoreactive Amino-Terminal Pro-Brain Natriuretic Peptide (NT-PROBNP), Protein S100-A8, Protein S100-A9, Alpha-1B-glycoprotein (A1BG), Beta-2-microglobulin (B2M), Calponin-1 (CNN1), Carbonic anhydrase (CA3), (Complement C4-A (C4A), Tenascin-X (TNXB), Pulmonary surfactant-associated protein C (SFTPC), Uteroglobin (SCGB1A1), Periostin (POSTN), Apolipoprotein A-II (APOA2), Collagen alpha-1(XIV) chain (COL14A1), Complement C3 (C3), Apolipoprotein A-1 (APOA1), Antithrombin-III (SERPINC1), von Willebrand factor (VWF), High mobility group protein B1 (HMGB1), Flavin reductase (NADPH) (BLVRB), Fibulin-1 (FBLN1), Heat shock protein beta-6 (HSPB6), BTB/POZ domain-containing protein (KCTD12), Zyxin (ZYX), Carbonic anhydrase 1 (CA1), Alcohol dehydrogenase 1B (ADH1B), Fibulin-5 (FBLN5), Neutrophil gelatinase-associated lipocalin (LCN2), Serpin H1 (SERPINH1), Periaxin (PRX), Protein S100-A12 (S100A12), Myeloblastin (PRTN3), Alpha-2-macroglobulin (A2M), Serotransferrin (TF), Histone H2B type 1 (HIST1H2BK), Isoform 2 of collagen alpha-1(XVIII) chain (COL18A1), Basement membrane-specific heparin sulfate proteoglycan core protein (HSPG2), Fibrillin-1 (FBN1), Bone marrow stromal antigen 2 (BST2), Matrix metalloproteinase-9 (MMP9), Periplakin (PPL), Serum amyloid A-1 (SAA1), Thrombospondin-1 (THBS1), Tubulin-specific chaperone A (TBCA), Serine-tRNA ligase, cytoplasmic (SARS), and Aldose reductase (AKR1B1).

In more specific aspects, the kit is provided as an ELISA kit comprising antibodies to at least one biomarker in a sample, wherein the at least one biomarker comprises Hepatoma Derived Growth Factor (HDGF). The ELISA kit may comprise a solid support, such as a chip, microtiter plate (e.g., a 96-well plate), bead, or resin having biomarker capture reagents attached thereon. The kit may further comprise a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP.

The kit for predicting or diagnosing PAH may be provided as an immunochromatography strip comprising a membrane on which the antibodies are immobilized, and a means for detecting the antibodies, such as gold particle bound antibodies. The types of membranes used are known in the art and include nitrocellulose and PVDF membranes. The kit may also comprise a plastic plate on which a sample application pad, gold particle bound antibodies temporally immobilized on a glass fiber filter, a nitrocellulose membrane on which antibody bands and a secondary antibody band are immobilized and an absorbent pad are positioned in a serial manner, so as to keep continuous capillary flow of blood serum.

In certain aspects, a patient can be diagnosed by adding blood or blood serum from the patient to the kit and detecting the relevant biomarkers conjugated with antibodies. The method may comprise the steps of collecting blood or blood serum from a patient, separating blood serum from the patient's blood, adding the blood serum from the patient to a diagnostic kit, and detecting the biomarkers conjugated with antibodies. If the biomarkers are present in the sample, the antibodies will bind to the sample, or a portion thereof. In other kit and diagnostic aspects, blood or blood serum need not be collected from the patient because it is already collected.

In other aspects, the kit can also comprise a washing solution or instructions for making a washing solution, in which the combination of the capture reagents and the washing solution allows capture of the biomarkers on the solid support for subsequent detection by, for example, antibodies or mass spectrometry. In further aspects, a kit can comprise instructions in the form of a label or separate insert. For example, the instructions may give information regarding how to collect the sample, how to wash the probe, or the particular biomarkers to be detected, and the like. In yet another aspect, the kit can comprise one or more containers with biomarker samples that can be used as standard(s) for calibration.

VII. Methods of Treatment

In still other aspects, the methods of the presently disclosed subject matter further comprise methods of treatment. These methods include informing the patient or a treating physician of the susceptibility of the patient to PAH. In other aspects, the methods further comprise informing the patient or a treating physician of the susceptibility of the patient to PAH. In still other aspects, the patient is undergoing PAH therapy, e.g., a vasodilator therapy, and the methods further comprise informing the patient or treating physician of the effectiveness of the PAH therapy, e.g., a vasodilator therapy. The treating physician is meant to refer to a physician who diagnoses and/or monitors the patient. The physician may be a general practitioner or a physician who specializes in diseases or disorders related to PAH.

Based on the results of the presently disclosed subject matter, further procedures may be indicated, including additional diagnostic tests or therapeutic procedures. Accordingly, in another aspect, the methods of the presently disclosed subject matter further comprise a step of treating a subject having PAH. In a particular aspect, the step of treating a subject having PAH comprises administering a therapeutically effective amount of a PAH therapeutic agent, e.g., a vasodilator, to the subject having PAH.

As used herein, the terms "treat," treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. It will be appreciated that, although not precluded, treating a disease, disorder or condition does not require that the disease, disorder, condition or symptoms associated therewith be completely eliminated.

The vasodilators may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20$^{th}$ Ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the vasodilators may be formulated and diluted in aqueous solutions, such as in physiologically compatible buffers, such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the vasodilators into dosages suitable for systemic administration is within the scope of the disclosure. With proper choice of carrier and suitable manufacturing practice, the vasodilators may be formulated as solutions and may be administered parenterally, such as by intravenous injection. The vasodilators can be formulated readily using pharmaceutically acceptable carriers well known in the art into dosages suitable for oral administration. The vasodilators can be administered as tablets, pills, capsules, liquids, gels, syrups, slurries, suspensions and the like, for oral ingestion by a subject (e.g., patient) to be treated.

For nasal or inhalation delivery, the vasodilators may be formulated by methods known to those of skill in the art, and may include, for example, but not limited to, examples of solubilizing, diluting, or dispersing substances, such as, saline, preservatives, such as benzyl alcohol, absorption promoters, and fluorocarbons.

In addition to the active ingredients, the vasodilators may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the vasodilators with solid excipients, optionally grinding a resulting mixture, and processing the mixture of granules, after adding suitable auxiliaries, if desired, to obtain tablets or dragee cores. Suitable excipients are, in particular, fillers, such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethylcellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof, such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler, such as lactose, binders, such as starches, and/or lubricants, such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

VIII. General Definitions

Unless defined otherwise, all technical and scientific terms used herein have the meaning commonly understood by a person skilled in the art to which this invention belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some aspects, ±100% in some aspects±50%, in some aspects±20%, in some aspects±10%, in some aspects±5%, in some aspects±1%, in some aspects±0.5%, and in some aspects±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative aspects of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Using a non-biased proteomics discovery approach, HDGF was identified as a protein that was increased 4 fold by MS peptide counts (FIG. 1A) in the lungs of patients with either APAH-CHD (pulmonary hypertension associated with congenital heart disease) or IPAH (idiopathic pulmonary hypertension) and >40 fold in plasma of IPAH as compared to control. To pursue HDGF as a possible circulating biomarker and as no HDGF assay exists, a high sensitivity sandwich chemilluminescent ELISA (Meso Scale Discovery) was developed using a combination of laboratory developed polyclonal (T2-21) (Everett et al. (2000) *J. Clin. Invest.* 105:567-575; Everett et al. (2001) *J. Biol. Chem.* 276:37564-37568; Everett et al. (2004) *Am. J. Physiol. Lung* 286:L1194-1201; Narron et al. (2006) *Peds. Res.* 59:778-783)/monoclonal (2F12) (Zhanga et al. (2010) *J. Immunological Methods* 355:61-67) antibodies and bacterial expressed recombinant protein, yielding an assay with an LLOD of 0.04 ng/mL. Plasma was assayed from age and sex matched normal controls (N=30), and PAH samples from the Pulmonary Hypertension Breakout Initiative (PHBI, patients with severe PAH, enrolled prior to lung transplant) IPAH (N=25) and APAH (N=17) samples. As shown in the FIG. 1A and FIG. 1B, median levels of HDGF were approximately 40 fold higher in IPAH and APAH samples as compared to controls (P<0.0001). Of importance, the median plasma HDGF value for normal was below the lower limit of quantification and at the lower limit of detection. Therefore the presently disclosed subject matter provides HDGF as a new plasma PAH biomarker.

To further test whether circulating HDGF concentrations predict PAH survival, a cohort of 73 PAH patients (IPAH and APAH-CTD) from the JHU Adult PAH Program (Paul Hassoun, Table 1) with a median follow up of 2.5 years (range 0.09-7.2 years) was assayed. The mean and range for both NT-proBNP and HDGF are shown as well as functional status (NYHA class and 6MWD), and hemodynamics. As shown in FIG. 2A and FIG. 2B, compared with healthy controls (median HDGF 0.145 ng/mL, N=60), the circulating HDGF concentration (median 0.815 ng/mL, N=74, p=0.0003) at enrollment was significantly higher in aggregate and PAH subgroups (Panel B). HDGF was significantly increased in the IPAH (median 0.633 ng/mL, N=36, p=0.0005) and SScPAH (median 1.01 ng/mL, N=37, p<0.0001). As shown in FIG. 3, HDGF has a significant ROC curve for predicting survival in this cohort of 0.71. The current standard of care PAH biomarker is NT-proBNP (Souza et al. (2007) *Resp. Med.* 101:69-75). As shown in FIG. 4, there was no difference between the HDGF and NT-proBNP ROC for predicting survival (P=0.66).

Using a HDGF cutpoint from the ROC curve (FIG. 3) of 0.426 ng/mL gives a significant (P=0.02) unadjusted Cox Hazard Ratio (HR) of 3.7 (95% CI 1.5-8.7) (FIG. 5). When HDGF was adjusted for NT-proBNP at the 0.426 ng/mL cutpoint, the Cox HR increased 4.5 (95% 1.02 to 20.1) (FIG. 6). This data demonstrates that HDGF is a significant PAH diagnostic and prognostic biomarker and is at least equivalent to NT-proBNP for predicting survival.

As shown in Table 2, when PAH patients were divided into low-HDGF (<0.426 ng/mL) and high-HDGF (>0.426 ng/mL). The high-HDGF group was significantly associated with a shorter 6 min walk test (6 MWD). Currently this is the gold standard for determining drug therapeutic efficacy in PAH. Importantly high-HDGF was not associated with right pressures (RAP, mPAP) or resistance, or cardiac output/index (CO and CI). These results indicate that HDGF concentrations are associated with a positive therapeutic drug response and independent of heart pressures or function, unlike NT-proBNP.

TABLE 1

Demographics and Characteristics

| Demographics | | |
|---|---|---|
| n = | 73 | |
| Age (years) | 59.9 ± 13.6 | |
| Female (n, %) | 58 (80%) | |
| Race- EA, AA, other n (%) | 61/10/2 (83/13.6/0.3%) | |
| IPAH/CTD-PAH n, (%) | 36/37 (49/51%) | |
| 6 MWD (m) | 383 | Range 211-671 |
| NYHA-FC | n = | % |
| I (10) | | 13.7 |
| II (31) | | 42.5 |
| III (28) | | 38.4 |
| IV (4) | | 0.5 |
| Laboratory Chemistries | | |
| NT-proBNP (pg/ml) | 2089 | Range 20-11698 |
| HDGF (ng/ml) | 2.1 | Range 0.1-21.8 |
| Hemodynamics | | |
| RAP (mmHg) | 8.1 ± 4.7 | |
| mPAP (mmHg) | 43.9 ± 14.3 | |
| PCWP (mmHg) | 10.6 ± 3.9 | |
| PVR (WU) | 9.8 ± 6.5 | |
| CO (L min−1) | 4.7 ± 1.7 | |
| CI (L min$^{-1/m-2}$) | 2.6 ± 0.8 | |

Data expressed as mean and standard deviation (SD), number (n), percentage (%) or range as indicated.
Definitions of abbreviations:
EA = European American,
AA = African American,
RAP = right atrial pressure,
mPAP = mean pulmonary artery pressure,
PCWP = pulmonary capillary wedge pressure,
CO = Cardiac output,
CI = Cardiac index,
NYHA-FC = New York Heart Associated-Functional Class,
6 MWD = 6 Minute Walk Distance,
NT-proBNP = N-terminal pro-brain natriuretic peptide

TABLE 2

Clinical Characteristic as a Function of Serum HDGF

| | HDGF$_{low}$ n = 24 | HDGF$_{High}$ n = 49 | P-value |
|---|---|---|---|
| Demographics (Mean + SD) | | | |
| Age (years) | 55.1 + 15.0 | 62.2 + 12.4 | 0.04 |
| 6 MWD (m) (Range) | 413 + 102 | 366 + 98 | 0.04 |
| NYHA-FC (n/%) | | | |
| I | 4 (16.7) | 6 (12.2) | 0.2 |
| II | 13 (54.2) | 18 (36.7) | |
| III | 7 (29.2) | 21 (72.4) | |
| IV | 0 (0) | 4 (8.2) | |

TABLE 2-continued

Clinical Characteristic as a Function of Serum HDGF

| | HDGF$_{low}$ n = 24 | HDGF$_{High}$ n = 49 | P-value |
|---|---|---|---|
| Laboratory Chemistries (Mean and Range) | | | |
| NT-proBNP (pg/ml) | 1262 (39-6922) | 2562 (20-11698) | 0.07 |
| Hemodynamic (Mean ± SD) | | | |
| RAP (mmHg) | 9.6 + 5.7 | 7.5 + 4.2 | 0.16 |
| mPAP (mmHg) | 45.0 + 14.7 | 43.5 + 14.3 | 0.8 |
| PCWP (mmHg) | 11.8 + 3.7 | 9.7 + 3.8 | 0.01 |
| PVR (WU) | 9.7 + 5.5 | 9.8 + 7.0 | 0.4 |
| CO (L min−1) | 5.2 + 2.0 | 4.5 + 1.5 | 0.1 |
| CI (L min$^{-1/m-2}$) | 2.7 + 0.8 | 2.5 + .08 | 0.3 |

Data expressed as mean and standard deviation (SD), number (n), percentage (%) or range as indicated.
Definitions of abbreviations:
EA = European American,
AA = African American,
RAP = right atrial pressure,
mPAP = mean pulmonary artery pressure,
PCWP = pulmonary capillary wedge pressure,
CO = Cardiac output,
CI = Cardiac index,
NYHA-FC = New York Heart Associated-Functional Class,
6 MWD = 6 Minute Walk Distance,
NT-proBNP = N-terminal pro-brain natriuretic peptide Example 2

Proteomic Discovery of Pulmonary Hypertension Biomarker Hepatonoma Derived Growth Factor A non-cardiac blood based biomarker could enhance treatment monitoring and prognostication for pulmonary hypertension (PH). We investigated whether, like NT-proBNP, the diagnostic and prognostic value of hepatoma derived growth factor (HDGF) can be confounded by heart failure or chronic disease.

Using a cohort of Johns Hopkins Emergency Department (ED) patients with only left sided heart failure (N=17, tricuspid insufficiency jet<2.8 m/s) or chronic illnesses (DM, hypertension, hypercholesterolemia, obesity, or smoking, N=66), we investigated the association of HDGF with chronic disease and with NT-proBNP in pure left sided heart failure.

HDGF concentrations were significantly elevated in PH versus healthy controls (p=0.013), left sided heart failure (p=0.0026) or chronic disease (p=0.0002), but were not significantly different between healthy controls versus left sided heart failure (P=0.70) or chronic disease (P=0.29).

As shown in FIG. 7A, median HDGF values were not different from normal healthy controls (P=0.16). Although NT-proBNP was elevated in all of these patients with left heart failure (range 1760-30,261 ng/mL), there was no correlation with HDGF (R=0.01, P=0.97).

To begin to understand the specificity of HDGF for PAH, we analyzed the serum HDGF in a cohort (N=66) of patients with existing chronic non-heart failure cardiovascular conditions. As shown in FIG. 7B, HDGF serum concentrations were not significantly different from the healthy control cohort (P=0.906).

Currently, the cardiac peptide NTproBNP is the state-of-the-art biomarker for PAH; however, it is developmentally regulated and confounded by systemic disease, more importantly it is not lung/vascular specific. Statistical analysis indicated that HDGF has similar power to determine survival in PAH patients, but the origin of these biomarkers may provide different information for PAH pathobiology. To begin to determine the origin of circulating HDGF in PAH, we evaluated HDGF protein expression levels in mouse lung and heart (left ventricle) tissues using western blotting. As shown in FIG. 8., HDGF expression was abundant in lung, but very low in cardiac tissue.

The data demonstrate that HDGF is a novel non-cardiac PH biomarker equivalent to NT-proBNP, not confounded by left sided heart failure and significantly associated with 6MWD, the single most important clinical functional measure in PH. Thus, HDGF may add additional value in PH risk stratification for clinical trials as well as future PH drug development.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Although the foregoing subject matter has been described in some detail by way of illustration and example for purposes of clarity of understanding, it will be understood by those skilled in the art that certain changes and modifications can be practiced within the scope of the appended claims.

HDGF, wherein the detection is indicative that the subject has or is susceptible to developing PAH.

2. The method of claim 1, further comprising informing the subject or a treating physician of the susceptibility of the subject to PAH.

3. The method of claim 1, wherein the method further comprises a step of administering a therapeutically effective amount of a PAH therapeutic agent to the subject having PAH.

4. The method of claim 3, wherein the PAH therapeutic agent is a vasodilator.

5. The method of claim 1, further comprises detecting at least one biomarker in combination with HDGF, wherein the substrate of step (a) further comprises an antibody specific for the at least one biomarker, and wherein detecting step (b) further comprises a monoclonal antibody specific for the at least one biomarker.

6. The method of claim 5, wherein the at least one biomarker comprises one or more biomarkers selected from the group consisting of Immunoreactive Amino-Terminal Pro-Brain Natriuretic Peptide (NT-PROBNP), Protein S 100-A8, Protein S100-A9, Alpha-1B-glycoprotein (AMG), Beta-2-microglobulin (B2M), Calponin-1 (CNN1), Carbonic anhydrase (CA3), (Complement C4-A (C4A), Tenascin-X (TNXB), Pulmonary surfactant-associated protein C (SFTPC), Uteroglobin (SCGBIAI), Periostin (POSTN), Apolipoprotein A-II (APOA2), Collagen alpha-1(XIV) chain (COL14A1), Complement C3 (C3), Apolipoprotein A-1 (APOA1), Antithrombin-III (SERPINC1), von Willebrand factor (VWF), High mobility group protein B1 (HMGB1), Flavin reductase (NADPH) (BLVRB), Fibulin-1 (FBLN1), Heat shock protein beta-6 (HSPB6), BTB/POZ domain-containing protein (KCTD 12), Zyxin (ZYX), Carbonic anhydrase 1 (CA1), Alcohol dehydrogenase IB (ADH1B), Fibulin-5 (FBLN5), Neutrophil gelatinase-associated lipocalin (LCN2), Serpin HI (SERPINH1), Periaxin (PRX), Protein SI 00-A12 (S 100A12), Myeloblasts (PRTN3), Alpha-2-macroglobulin (A2M), Serotransferrin (TF), Histone H2B type 1 (HIST1H2BK), Isoform 2 of collagen alpha-1 (XVIII) chain (COL18A1), Basement membrane-specific heparin sulfate proteoglycan core protein (HSPG2), Fibrillin-1 (FBN1), Bone marrow stromal antigen 2 (BST2), Matrix metalloproteinase-9 (MMP9), Periplakin (PPL), Serum amyloid A-1 (SAA1), Thrombospondin-1 (THBS1), Tubulin-specific chaperone A (TBCA), Serine-tRNA ligase, cytoplasmic (SARS), and Aldose reductase (AKRIB I).

7. The method of claim 1, wherein the sample is selected from the group consisting of lung tissue, blood, plasma, saliva, urine, and serum.

---

---

That which is claimed:

1. A method for predicting or diagnosing pulmonary artery hypertension (PAH) in a subject having PAH, at risk of having PAH, or suspected of having PAH, the method comprising:
(a) contacting a sample from a subject at risk of having or suspected of having PAH with an antibody bound to a substrate, wherein the antibody specifically binds SEQ ID NO:1;
(b) detecting an elevated level of expression of Hepatoma Derived Growth Factor (HDGF) relative to a control with a monoclonal antibody that specifically binds 8. The method of claim 1, wherein the pulmonary artery hypertension (PAH) is selected from the group consisting of idiopathic pulmonary artery hypertension (IP AH), associated pulmonary artery hypertension (APAH), PAH caused by structural heart disease, PAH caused by lung disease, PAH caused by inflammatory disease, PAH caused by heart failure, PAH caused by congenital heart disease, and PAH in a newborn.

9. The method of claim 1, wherein the elevated level comprises at least a 1.5 fold difference between the level of HDGF in the sample and the control.

10. The method of claim 1, wherein the antibody of the contacting step (a) comprises a polyclonal antibody.

11. The method of claim 1, wherein the monoclonal antibody of step (b) is the antibody designated 2F12.

12. The method of claim 1, wherein the detecting step (b) comprises electrochemiluminescent detection.

* * * * *